United States Patent
Heinen

(10) Patent No.: US 8,974,481 B2
(45) Date of Patent: Mar. 10, 2015

(54) INSTRUMENT FOR PRODUCING A SKIN OPENING FOR MINIMALLY INVASIVE SURGERY

(75) Inventor: Josef Heinen, Nettetal (DE)

(73) Assignee: Gimmi GmbH, Tuttlingen (DE)

( * ) Notice: Subject to any disclaimer, the term of this patent is extended or adjusted under 35 U.S.C. 154(b) by 563 days.

(21) Appl. No.: 11/743,543

(22) Filed: May 2, 2007

(65) Prior Publication Data

US 2007/0260274 A1    Nov. 8, 2007

(30) Foreign Application Priority Data

May 2, 2006    (DE) .......................... 10 2006 020 595

(51) Int. Cl.
*A61B 17/34*    (2006.01)
*A61B 17/3209*    (2006.01)
*A61B 19/00*    (2006.01)

(52) U.S. Cl.
CPC ....... *A61B 17/3417* (2013.01); *A61B 17/32093* (2013.01); *A61B 2017/3454* (2013.01); *A61B 2019/306* (2013.01)
USPC ...................................................... 606/185

(58) Field of Classification Search
CPC ..................... A61B 17/3417; A61B 17/32093; A61B 2017/3454; A61B 2019/306
USPC .......... 604/117; 606/167, 170, 172, 181, 184, 606/185, 186; 30/151, 162, 358, 360, 30/366–368
See application file for complete search history.

(56) References Cited

U.S. PATENT DOCUMENTS

| | | | | |
|---|---|---|---|---|
| 3,645,268 A | * | 2/1972 | Capote .......................... | 604/117 |
| 3,750,667 A | * | 8/1973 | Pshenichny et al. .......... | 604/117 |
| 4,633,860 A | * | 1/1987 | Korth et al. ................... | 606/170 |
| 4,955,890 A | * | 9/1990 | Yamamoto et al. ........... | 606/108 |
| 5,275,583 A | * | 1/1994 | Crainich ........................ | 604/264 |
| 5,385,572 A | * | 1/1995 | Nobles et al. ................. | 606/185 |
| 5,575,804 A | | 11/1996 | Yoon | |
| 5,607,440 A | * | 3/1997 | Danks et al. .................. | 606/185 |
| 5,688,246 A | | 11/1997 | Waitz et al. | |
| 5,843,108 A | * | 12/1998 | Samuels ........................ | 606/167 |
| 5,843,115 A | * | 12/1998 | Morejon ........................ | 606/185 |
| 6,136,014 A | * | 10/2000 | Sirimanne et al. ............ | 606/185 |
| 6,187,022 B1 | * | 2/2001 | Alexander et al. ............ | 606/185 |
| 6,716,201 B2 | * | 4/2004 | Blanco .......................... | 604/274 |
| 2002/0026207 A1 | * | 2/2002 | Stellon et al. ................. | 606/185 |

(Continued)

FOREIGN PATENT DOCUMENTS

| | | |
|---|---|---|
| DE | 27 43 336 A1 | 3/1979 |
| FR | 2 595 237 | 9/1987 |

(Continued)

OTHER PUBLICATIONS

Canadian Intellectual Property Office, "Office Action" in Canadian Patent Application No. 2,587,007, Document of 3 pages, dated Jan. 9, 2013.

*Primary Examiner* — David Eastwood
(74) *Attorney, Agent, or Firm* — Akerman LLP; Peter A. Chiabotti

(57) ABSTRACT

For producing a skin opening for minimally invasive surgery an instrument is employed, comprising a grip (10) and a puncture awl (16). The puncture awl (16) is provided on the distal end of a grip (10), which distal end forms a stop surface (12), which limits the penetration depth of the puncture awl (16).

6 Claims, 2 Drawing Sheets

(56) References Cited

U.S. PATENT DOCUMENTS

| | | | |
|---|---|---|---|
| 2002/0133188 A1* | 9/2002 | O'Heeron et al. | 606/185 |
| 2002/0161387 A1* | 10/2002 | Blanco | 606/185 |
| 2002/0193806 A1* | 12/2002 | Moenning et al. | 606/108 |
| 2003/0073960 A1* | 4/2003 | Adams et al. | 604/268 |
| 2005/0177183 A1* | 8/2005 | Thorne et al. | 606/167 |
| 2006/0030870 A1* | 2/2006 | Staudner | 606/167 |
| 2006/0276772 A1* | 12/2006 | Moos et al. | 604/506 |

FOREIGN PATENT DOCUMENTS

| | | |
|---|---|---|
| GB | 2199247 | 7/1988 |
| GB | 2 400 324 A | 10/2004 |

\* cited by examiner

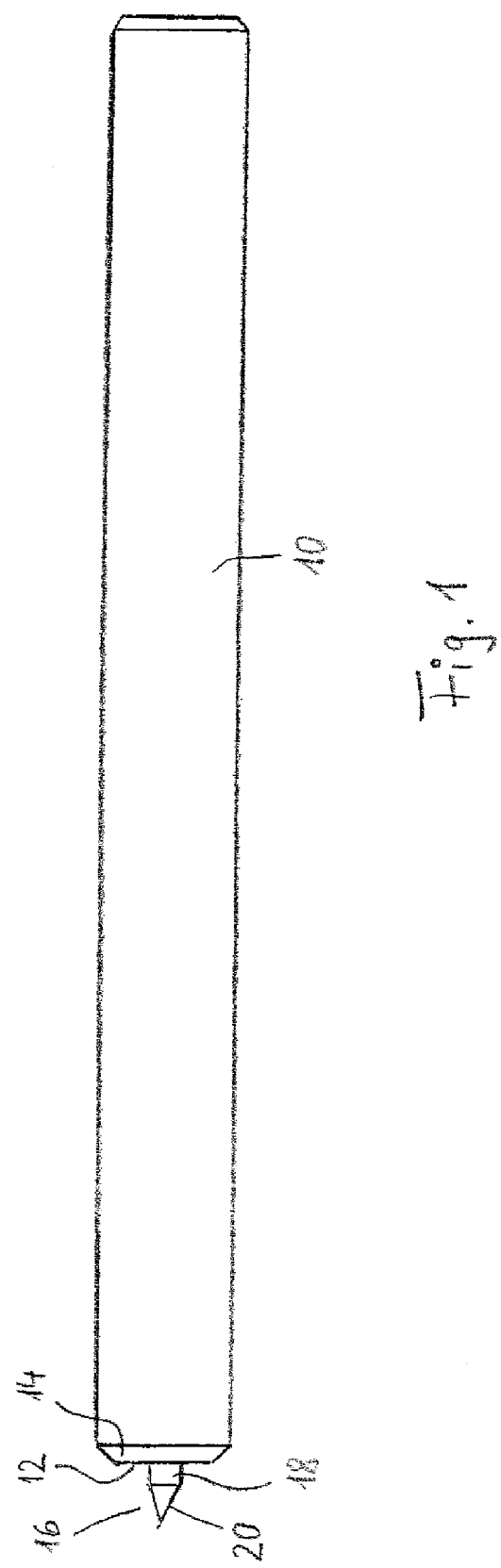

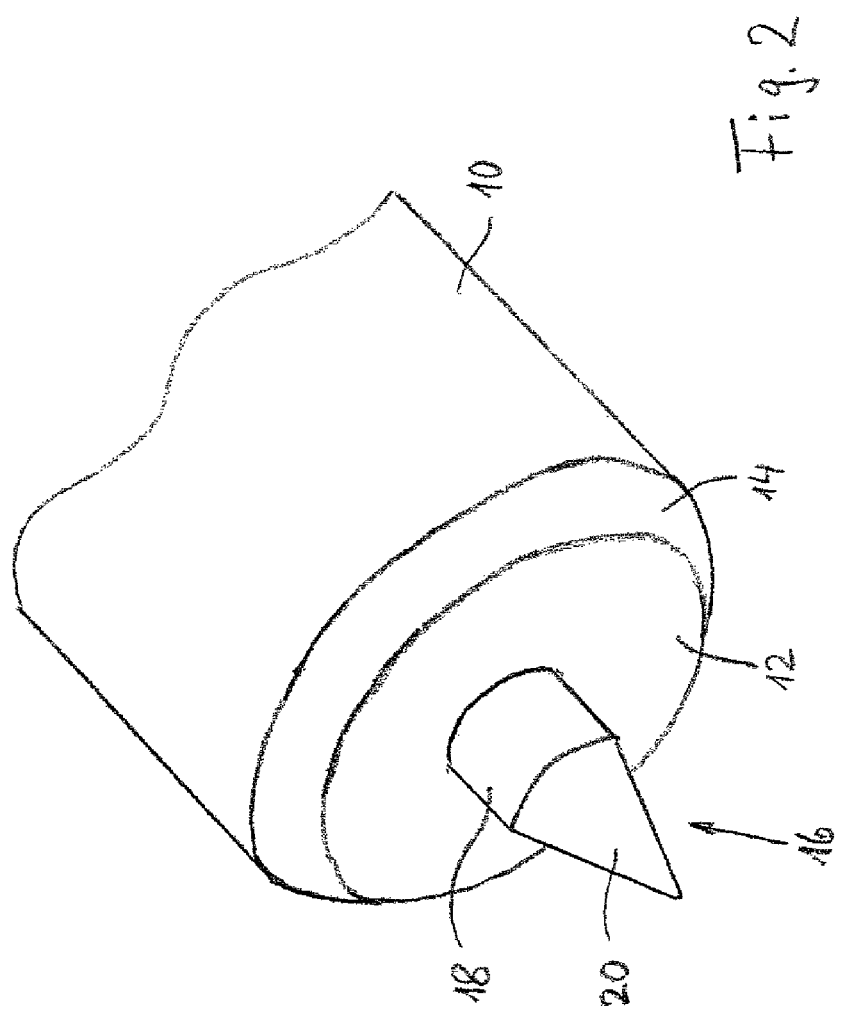

INSTRUMENT FOR PRODUCING A SKIN OPENING FOR MINIMALLY INVASIVE SURGERY

FIELD OF THE INVENTION

The invention concerns an instrument for producing a skin opening for minimally invasive surgery, an instrument set for producing access for minimally invasive surgery, as well as a process for producing an access for minimally invasive surgery.

BACKGROUND OF THE INVENTION

For a large number of surgical interventions the so-called minimally invasive surgery has become established. In this operation technique access to the field of operation lying within the body of the patient is obtained using a trocar sheath, through which surgical instruments, optical systems and the like can be introduced into the body. The advantage of this operation technique is comprised in particular therein, that the skin, and in certain cases thereunder lying tissue muscle layers, need only be opened a relatively small amount, so that only small operation wounds result. Thereby the pain associated with the operation wound is reduced, a more rapid healing is possible, and smaller operation scars result.

In order to be able to use the trocar sheath as an access way to the intracorporal field of operation, it is necessary to first produce an opening in the skin. For this, an incision is made using a scalpel, and the tissue below the skin in separated. This cut conventionally has a length of 10 to 15 mm, and represents an operation wound which must heal and can lead to scarring.

The invention is concerned with the task of further reducing the opening of the body surface for minimally invasive surgery.

SUMMARY

This task is inventively solved by an instrument, instrument set and by a process as described herein.

In accordance with the invention, the skin opening for the introduction of the trocar sheath is not produced by an incision using a scalpel. Rather, an instrument with a puncture awl or spur is used. The puncture awl is located distally on a grip, wherein the distal end of the grip, upon which the puncture awl is provided, forms a stop surface. The puncture awl has an axial length of approximately 5 to 10 mm. Distally the puncture awl terminates in a tip and widens in diameter towards its end bordering the stop surface to an approximate maximal diameter of 2 to 3 mm.

For opening the skin the puncture awl is stabbed into the skin, so that a hole is produced in the skin, of which the diameter corresponds to the maximal outer diameter of the puncture awl. The depth of the puncture hole is limited in that the stop surface of the grip contacts the skin surface and therewith a further penetration of the puncture awl is prevented. The maximal penetration depth is therewith determined by the axial length of the puncture awl. The depth of the produced puncture hole is actually greater than the axial length of the puncture awl, which is a consequence thereof, that the skin and the tissue layers lying under the skin are compressed by the axial pressure of the stop surface. The axial length of the puncture awl is approximately 5 to 10 mm, whereby a depth of the puncture hole of approximately 10 to 15 mm results. The puncture depth is sufficient to penetrate the puncture resistant epidermis and to provide an opening for the introduction of a trocar sheath and trocar or an obturator. A damaging of the vessels underlying the epidermis or organs underlying the skin is precluded by limiting of the penetration depth. The tissue layers lying under the epidermis offer less resistance, so that they can be penetrated by the sharp tipped trocar sheath or, as the case may be, by a blunt tipped obturator, if these are to be inserted into the epidermis through the penetration hole.

The diameter of the penetration hole produced using the penetration awl corresponds maximally to the maximal diameter of the penetration awl and is thus approximately 2 to 3 mm. The trocar sheath is introduced through this puncture hole, in which case a pointed trocar or a blunt obturator is situated for penetration of the tissue. The outer diameter of the trocar sheath is at least as large as the diameter of the puncture awl or, as the case may be, the skin opening produced thereby. Preferably the outer diameter of the trocar sheath is somewhat larger than the maximal diameter of the puncture awl, preferably approximately 0.5 mm larger, and maximally approximately 1 mm larger. Thereby the skin opening produced by the puncture awl is dilated by introduction of the trocar sheath, wherein the widening of the skin opening essentially occurs by atraumatic displacement of the skin tissue. As the trocar sheath is removed again after conclusion of the operation, the skin opening can draw together elastically to the diameter of the original puncture hole produced by the puncture awl.

The inventive operation technique thus requires only a minimal puncture as the access way to the intracorporal operation field, which represents a substantial improvement in comparison to the incision by means of a scalpel. The small puncture hole is easier to close, and often a water-tight wound adhesive is sufficient to close the puncture hole following the operation. The minimal lesion of the puncture hole results in a very rapid healing, in which case wound-healing problems are practically precluded. The small wound surface reduces the penetration of microbes by at least approximately 50% in comparison to conventional minimally invasive operation techniques. The small puncture hole reduces the pain of the wound to a minimum. Cosmetically unappealing scar formation is reduced to a minimum.

BRIEF DESCRIPTION OF THE DRAWINGS

In the following the invention will be described in greater detail on the basis of an illustrative embodiment shown in the figures. There is shown in:

FIG. 1: an instrument according to the invention in side view, and

FIG. 2: an enlarged view of the distal end of the instrument.

DETAILED DESCRIPTION OF THE PREFERRED EMBODIMENTS

The instrument includes a grip 10 which is elongated axially. In the illustrative embodiment the grip is similar to a pencil and has a generally cylindrical shape. The diameter of the grip 10 is so selected, that it is ergonomically comfortable to manipulate by hand. Accordingly, the grip 10 has a diameter of approximately 10 mm and an axial length of approximately 120 mm.

Of course the grip 10 can also have alternative shapes, in order to facilitate the manipulation of the instrument or to change the design. Accordingly, the cross section of the grip 10 need not be circular, but rather can be flattened, oval or polygonal. In the axial direction the grip 10 need not have constant diameter, but rather can have areas of narrowed and widened diameter. The surface of the grip 10 can be structured or textured, for example with circumscribing ridges, knurls, a roughening or the like.

The distal end surface of the grip 10 is in the form of a stop surface 12, which is perpendicular to the axis of the grip 10. The circumscribing edge of the contact surface 12 is reduced by a bevel 14.

Centrally in the stop surface 12, and therewith axially aligned with the center axis of the grip 10, a puncture awl 16 is provided, which projects axially in the distal direction and therewith perpendicular to the stop surface 12. The puncture awl 16 has an axial total length of approximately 5 to 8 mm. In its proximal area 18 adjacent the stop surface 12 the puncture awl is cylindrically shaped with a diameter of approximately 2 to 3 mm, preferably with a diameter of approximately 2.5 mm. In its distal area the puncture awl 16 transitions into a sharp tip 20, which narrows in the distal direction from the diameter of the proximal area 18. In the shown embodiment the tip 20 is conically shaped. It is of course possible that the tip 20 in its outer surface is bowed out spherically (convex) or shaped more tapered (concave). It is further possible that the tip 20 has a polygonal cross section, for example triangular or square. Finally, it is also possible that the cross section of the puncture awl 16 and in particular its proximal area 18 is not circular, but rather oval or polygonal.

The proximal area 18 and the tip 20 each respectively extend over approximately one half of the length of the puncture awl 16.

The grip 10 and the puncture awl 16 are preferably manufactured unitarily. As material, stainless steel is particularly preferred. Likewise, the instrument can be manufactured from plastic.

The invention claimed is:

1. A process for producing an access opening for minimally invasive surgery, comprising the steps of:
    piercing into skin with a puncture awl of an instrument, wherein the instrument is comprised of:
        a grip element having a proximal end and a distal end, wherein the grip element is generally cylindrically shaped and has a diameter between the proximal end and the distal end of the grip element;
        a beveled circumscribing edge positioned at the distal end of the grip element, the beveled circumscribing edge having a proximal end and a distal end, wherein the beveled circumscribing edge has a narrowing diameter between the proximal end and the distal end of the beveled circumscribing edge;
        a flat stop surface positioned at the distal end of the beveled circumscribing edge, the flat stop surface being perpendicular to a lengthwise axis of the grip element and the flat stop surface having a diameter that is larger than a largest diameter of the puncture awl; and
        the puncture awl unitarily formed with the grip element and having a generally cylindrically shaped proximal area extending distally and perpendicularly from the flat stop surface and further having a sharp tip that extends distally from the proximal area and narrows from a diameter of the proximal area, wherein the proximal area has a length that is approximately one half of a length of the puncture awl and the sharp tip has a length that is approximately one half of the length of the puncture awl, wherein the diameter of the proximal area is a constant diameter along the length of the proximal area; and
    inserting the puncture awl into the skin until the flat stop surface abuts against an external surface of the skin prohibiting further insertion such that only the puncture awl penetrates the skin and produces a puncture hole, in which a depth of penetration of the puncture awl is limited by the flat stop surface, the puncture hole providing an opening for introduction of a trocar sheath and trocar or an obturator into the puncture hole.

2. The process according to claim 1, wherein the puncture hole diameter is approximately 2.5 mm.

3. The process according to claim 1, further comprising the step of:
    compressing the skin in contact with the flat stop surface such that a depth of the puncture hole is greater than the length of the puncture awl.

4. The process according to claim 1, wherein the produced puncture hole has a diameter of approximately 2 to 3 mm, in which the depth of penetration of the puncture awl is limited to approximately 10 mm.

5. The process according to claim 1, wherein the diameter of the proximal area of the puncture awl is approximately 2 to 3 mm, and the diameter of the grip element is approximately 10 mm.

6. The process according to claim 1, further comprising stabbing the puncture awl into the skin.

* * * * *